United States Patent [19]

Leary et al.

[11] 4,453,151
[45] Jun. 5, 1984

[54] SEMICONDUCTOR GAS SENSOR

[76] Inventors: David J. Leary, 2832 Eagle Dr., Fort Collins, Colo. 80526; James O. Barnes, 3100 Rockwood Dr., Fort Collins, Colo. 80525

[21] Appl. No.: 385,822

[22] Filed: Jun. 7, 1982

[51] Int. Cl.³ .................. G01N 27/12; G01N 27/04; G01N 27/16
[52] U.S. Cl. ........................ 338/34; 73/23; 73/27 R; 422/90; 422/98; 436/121
[58] Field of Search .................. 338/34; 436/121; 422/90, 98; 73/23, 26, 27 R; 340/633, 634

[56] References Cited

U.S. PATENT DOCUMENTS

| | | | |
|---|---|---|---|
| 4,013,943 | 3/1977 | Chou et al. | 340/634 X |
| 4,197,089 | 4/1980 | Willis et al. | 340/634 X |
| 4,338,281 | 7/1982 | Treitinger et al. | 338/34 X |
| 4,347,732 | 9/1982 | Leary | 338/34 X |
| 4,387,165 | 7/1983 | Youngblood | 436/121 |

FOREIGN PATENT DOCUMENTS 59557 9/1982 European Pat. Off. ............ 422/98

Primary Examiner—B. A. Reynolds
Assistant Examiner—Christopher N. Sears
Attorney, Agent, or Firm—Jerry W. Berkstresser; Bruce G. Klaas

[57] ABSTRACT

A semiconductor gas sensor for use in equipment for detecting small amounts of $H_2S$. The method of sensor fabrication comprises spray deposition of a mixture of metal oxides mixed together with various metal and non-metal materials which serve in the finished product as activators, dopants, and/or film binder materials, and including in suspension a molecular sieve material, for enhancing and defining porosity on a scale of molecular dimensions in the finished sensor. All of the foregoing materials are suspended in a suitable solution and preferably sprayed onto a heated insulating substrate to form the finished product. The example sensor, capable of selective detection of $H_2S$ in air and a sensitivity of less than 1 PPM (part per million), is comprised of a platinum activated alumina, tin oxide, and zeolite molecular sieve material.

7 Claims, 2 Drawing Figures

SEMICONDUCTOR GAS SENSOR

FIELD OF THE INVENTION

This invention relates to semiconductor gas sensors and to methods of fabrication thereof, and more particularly to a unique spray deposition method wherein an improved semiconductor sensor is fabricated which comprises preselected gas sensor components in combination with a molecular sieve material to enhance and define porosity in the final semiconducting film. A specific example of a sensor and its method of fabrication is described which is capable of a selective detection of $H_2S$ by changes in the conductivity of the sensor relative to the concentration of $H_2S$ in the gas sample.

BACKGROUND OF THE INVENTION

Various semiconducting metal oxides have been used in conjunction with a variety of metal and non-metal additives in the fabrication of gas sensitive films suitable for use in gas detection apparatus. Exposure of such gas sensitive films to the gas of interest generally is detected as a change in conductivity of the film. In general, these prior devices exhibited inherent deficiencies in sensitivity, selectivity, response and recovery times, and/or calibration stability. The electrical characteristics and subsequent gas response characteristics of such materials when employed as gas sensors in previous gas sensing equipment have been found to be highly dependent upon film properties such as thickness, uniformity of composition, purity, film porosity, and density. Since it has previously been difficult to adequately control the foregoing factors this art has been seeking a technique of fabrication which would be capable of producing films with the above mentioned and other properties well controlled. In addition it is of course desireable that any new technique should be reproducible and cost effective. Further, the previous sensors were sometimes of limited utility if they were not capable of low temperature operation. This property is advantageous when sensing flammable gases in that there would be a reduced hazard of flammable gas ignition by the operating sensor, as well as an increased realiability and sensor life, reduced sensor power requirements, and better compatibility with on-chip integrated signal processing circuitry.

The previous attempts to achieve the foregoing properties employed several deposition techniques for depositing the materials and combinations of materials found suitable for use in semiconducting gas sensors. Typically the fabrication methods employed have included sintering, vacuum evaporation, sputtering, chemical vapor deposition, pyrolytic spray deposition, and solution coating. Besides the previously mentioned drawbacks, each of the foregoing methods creates specific problems. For example, sintered films often lack sensitivity due to lack of porosity in the processed material. Vacuum evaporation, sputtering, and chemical vapor deposition processes are costly, and sometimes lack flexibility by making it difficult to properly control the introduction of certain dopants.

In practice, the spray pyrolysis techniques consist of spraying a solution containing a soluble salt of the cation of interest with the aid of a carrier gas, onto a heated substrate whereupon the solution undergoes a chemical reaction to form the resultant film. This process is characterized by relatively high substrate temperatures during deposition; e.g. several hundred degrees Centigrade. The lower limit of substrate temperature is dictated by the required chemical dissociation reaction. To be successful there must be complete dissociation of the salt and this reaction rate therefore imposes a limitation on the deposition rate.

During film formation, film uniformity can be critically influenced by spray turbulence, lateral gas flow across the substrate and boundary layer formation in the vicinity of the substrate itself. Substrate temperature control is also very critical for film uniformity. Care must be taken to minimize thermal shock which accompanies the spraying of the material onto the heated substrate. Other deposition parameters have also required close control. The carrier flow rate affects the size and velocity distribution of droplets in the spray which affects the dynamics of impingement. These and other factors inherent in this process have resulted in increased process complexity and cost. Additionally, resultant films produced by this process are generally characterized by the presence of large grain sizes which results in low resistivity which further limits their usefulness for gas sensing applications. The process is also limited in its application to only those materials which can undergo the appropriate dissociation reaction, to produce the desired product on the heated substrate.

Solution coating techniques are more widely used for gas sensor fabrication because of the simplicity of the process and suitability of the film properties. Small grain size films of high porosity are possible to achieve. A solution containing the materials in suspension and/or in the form of a soluble salt is applied by brush or dipping to a suitable heated substrate where at a temperature of typically 100 degrees C. to 200 degrees C. the volatile components are driven off. The resultant substrate and film are then partially sintered by firing at a higher temperature typically 600 degrees C. to 800 degrees C. Enhanced film porosity is often achieved by addition of materials which volatilize and evaporate from the film during high temperature firing. Examples of such materials are starch, wax, stearic acid, and silica gel.

The solution coating process is operator intensive and technique sensitive. For these reasons solution coating is not suitable for batch processing and does not produce uniform product. For example, film thickness, grain size, chemical composition uniformity and porosity, all can vary which results in non-uniform gas sensing properties within the film and from sensor to sensor. Further, certain desireable additives, particularly transition metals such as platinum or palladium introduced to the source solution as soluble organometallic salts, have the tendency to precipitate out of or localize within a static solution, presumably because of solubility limits or due to chemical reaction and are therefore difficult to use when attempting to make a uniform product. Additionally, contamination in the final film by the anion of the soluble salt is an undesired result in both solution coating and pyrolytic spray processes.

Sensor materials which have been used in the past for gas sensitive films include a number of semiconducting metal oxides, such as $SnO_2$, $ZnO$, $Fe_2O_3$, $Al_2O_3$, $Ga_2O_3$, and $In_2O_3$. Examples of combinations of these materials with other materials for specific gas sensing applications are presented in the patent issued to Barry Bott Feb. 11, 1975, U.S. Pat. No. 3,865,550. The theory of operation generally proposed for these materials involves an electrochemical reaction of the gas with the solid surface of the heated sensor. The result of this reaction is to produce a charge transfer wherein an increase or decrease in the number of mobile carriers in the material takes place. In such a way, the conductivity in surface layers and at intergrannular contacts in the film is changed. This is measured usually as a change in conductance proportional to the gas concentration. Accordingly, it is highly desirable for sensors to have a large film surface area to volume ratio in order to exhibit the requisite sensitivity. While previous sensors with a high degree of porosity have had high sensitivity, such devices inherently are not selective and require operation at elevated temperatures usually above 250 degrees C. to preserve acceptable response and recovery times.

Boardman, Jr. et al. U.S. Pat. No. 3,901,067 issued Aug. 26, 1975, have described a sensor for selective detection of $H_2S$ in air. This sensor has been shown to operate selectively at somewhat lower temperature and within a narrow range. Other similar thin film sensors are commercially available. Such sensors generally suffer from poor response and recovery times, generally on the order of several minutes. When operated at higher temperatures, sensors of this type become electrically unstable, lose selectivity, and are short-lived.

None of the above sensors combine desireable characteristics of fast response and recovery times with selectivity and stability at low operating temperatures. Response times of a few seconds and comparable recovery times are necessary for most gases, particularly $H_2S$ because of its toxicity.

Where fast response and recovery times are achieved at higher operating temperatures (above the temperatures where thin film sensors usually operate), film stability considerations become more important. Thick film sensors fabricated by solution coating processes generally satisfy stability requirements. Sensitivity in these films is enhanced by a high degree of film porosity. However, selectivity has previously been lacking in thick film sensors.

OBJECTS OF THE INVENTION

It is therefore an object of the present invention to provide a process for fabricating semiconductor gas sensors that is low cost yet flexible in nature and which readily lends itself to batch processing.

It is yet another object of the present invention to provide a process for fabricating gas sensors which results in reproducible uniform films which comprise substantially the components of the original mixture in their same weight percent, uniformly distributed.

It is yet another object of the present invention to provide a relatively low temperature deposition process for gas sensor fabrication.

It is still another object of the present invention to provide a spray deposition process where no chemical reaction occurs during deposition on the substrate.

Further, it is an object of the present invention to provide a high sensitivity semiconducting gas sensor article fabricated by the process which is capable of selective detection of $H_2S$ in air with relatively fast response and recovery times and which operates with low heater power consumption.

SUMMARY OF THE INVENTION

It has been discovered that the above and further objects and advantages can be achieved when preselected gas sensor semiconductor materials are suspended in a carrier solution and spray deposited onto a heated insulating substrate which solution also contains a suspension of molecular sieve material in combination with the semiconducting materials. Preferably other materials are also suspended in the solution which act as activators, dopants and/or film binder materials in the finished sensor product. Selectivity of the finished sensor is enhanced when molecular sieve materials are incorporated into the final structure of the sensor. Zeolites, alumino-silicate structures whose molecular arrangement is such as to result in a porous structure with pores of molecular dimensions are typically used as molecular sieve materials. A range of zeolite materials with different pore sizes are commercially available. A given zeolite will have a discrete pore size and a very stable structure. The selectivity enhancement in semiconductor gas sensors incorporating these materials is not fully understood and without being bound by any specific theory, but it is believed that the sieve material acts in the finished article to define and enhance porosity in the finished films. Large gas molecules which otherwise might act as interferences may by virtue of the zeolite structure be effectively screened from the sensor materials, where as the smaller $H_2S$ molecule can enter the bulk of the solid sensor and contact the semiconductor sensor material. Further, the zeolites themselves are known to exhibit catalytic properties which may enhance the electro chemical reactions required for the conductivity change which is characteristic of the operation of a semiconductor sensor.

The semiconductor films of this invention prepared as described hereinafter therefore exhibit a high degree of defined porosity in a structure having good mechanical properties which will operate at relatively low temperatures with good selectivity and sensitivity together with fast response and recovery properties.

The spray deposition process of the present invention comprises spraying a solution of the herein described constituents suspended in powder form in an organic solvent or water or a mixture of the two. No chemical reaction at the substrate occurs, other than evaporation of the carrier solvent. The use of a low substrate temperature without the requirement of a chemical reaction, results in reduced susceptibility of the process to the control problems inherent in the pyrolytic spray process thus significantly reducing the process complexity and cost. The process of the present invention is flexible in that it is readily adapted to deposition of many materials combinations. Film reproducibility and uniformity are significantly enhanced compared with films produced by solution coating, and the present process permits incorporation of zeolites into the film which have been found to be highly desireable for producing sensors of improved selectivity and sensitivity. Further, single or multiple layered films of controlled thickness and desired porosity can now be reproducibly fabricated.

In the inventive process, the source material is prepared by mixing one or more metal-oxides in powder form with a metal or non-metal dopant and/or film binder and molecular sieve. The metal-oxide would be chosen from the many of those which have been demonstrated to possess gas responsive properties. The exact choice of metal-oxide to be used would be based on the gas to be sensed. Metal dopants are usually selected from among the transition metal group and act as activators or catalysts in promoting gas-solid electrochemical reactions. Film binding materials such as ceramic materials, have been incorporated in such sensors to improve film strength after post deposition anneal. Zeolite molecular sieve materials are commercially available with pore sizes ranging from about three angstroms to ten angstroms. The choice of zeolite would be based on the gas to be sensed. Preferably for sensing $H_2S$, five (5) angstrom material is used.

The materials selected are sized and mixed to the desired constituency usually by weight percent. Before weighing and mixing it is desireable to dehydration bake the powders for about 120 minutes at 115 degrees C. Heating during thorough mixing may also be necessary to minimize absorbed moisture related packing or clumping.

All or part of the resultant mixture is added to a liquid such as an organic solvent or water or any liquid or mixture of liquids that is capable of sustaining a solids in liquid suspension, so that the mixed powder is suspended in a carrier liquid that is suitable for spray deposition. Heating and/or stirring may be employed to assure uniform suspension of the material. In addition, suspension promoting agents may be added that do not deleteriously affect the final properties of the sensor.

Suitable substrates are positioned in the field of deposition and heated by either conduction or radiant heating. The lower limit of temperature must be high enough to accomplish the desired evaporation or gasification rate of the carrier liquid of the impinging solution and typically the preferred temperature employed will be in the range of 50 degrees C. to 150 degrees C. Any suitable carrier gas can be employed and air or nitrogen are preferred. The film deposition rate is controlled by the degree of dilution of the source solution, source solution flow rate, carrier gas velocity, and the physical configuration of the apparatus with its spray nozzle to substrate spacing. For a given deposition rate, the film thickness is determined by the duration of the deposition. Film thickness can be measured by interference techniques or any of a number of well known techniques. After deposition is complete, the substrates are removed and annealed at an elevated temperature usually in air to remove organic solvents and strengthen the film.

BRIEF DESCRIPTION OF THE DRAWING

An illustrative and presently preferred embodiment of the invention is shown in the accompanying drawing in which.

DETAILED DESCRIPTION OF THE DRAWING

Figure 1:
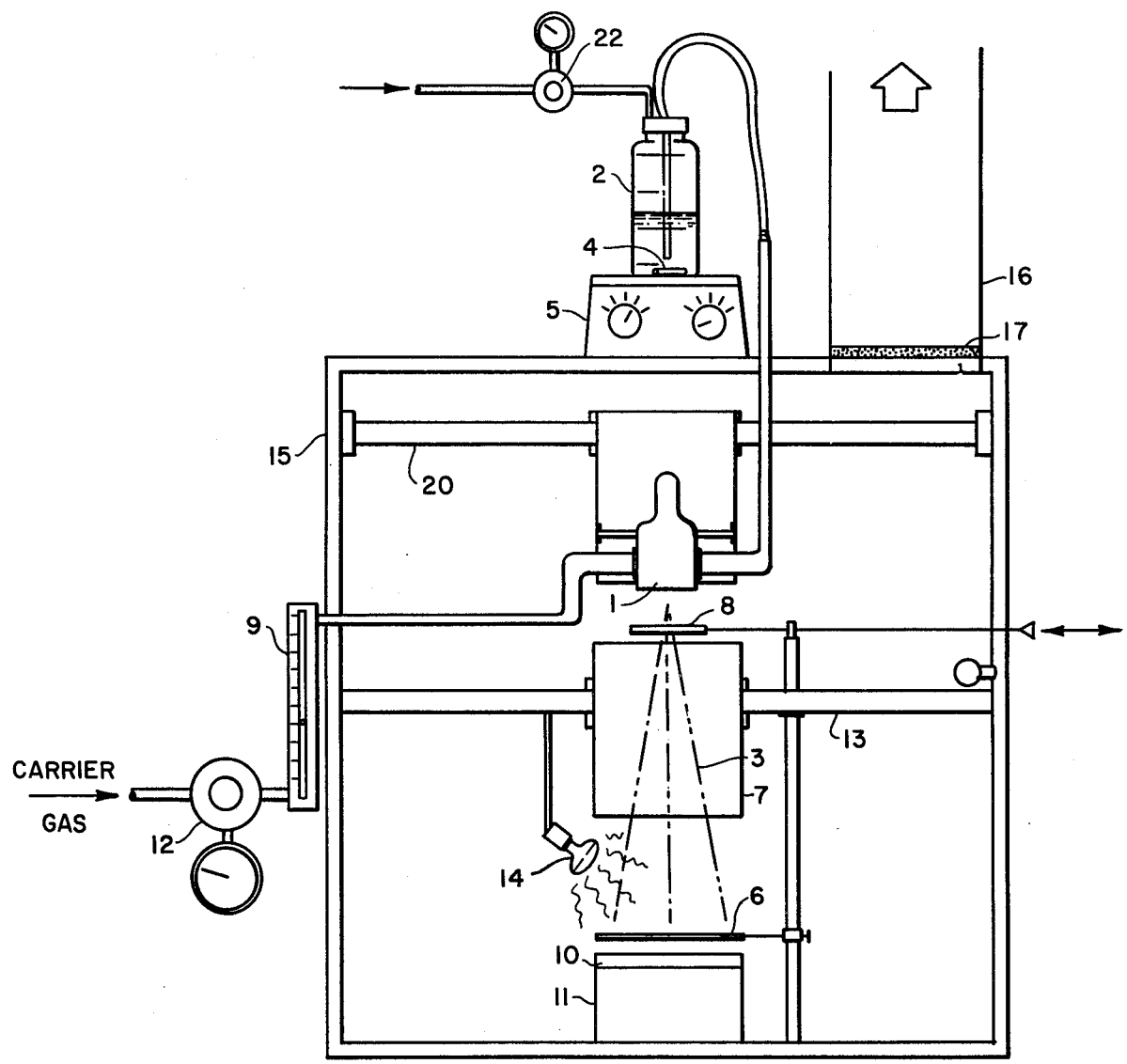
FIG. 1 is a diagrammatic illustration of a spraying apparatus used in the spray deposition of semiconductor films for gas sensors.

Reference should be made to FIG. 1 which is a diagrammatic illustration of a spraying apparatus useful in the spray deposition of semiconductor films for gas sensors according to this invention. The system comprises a spray nozzle 1 wherein a suitable carrier gas and the source solution mix and are sprayed so as to form a cloud of droplets of the solution, with a preselected velocity and spatial pattern, designated diagrammatically at 3. The source solution is contained in a bottle 2 and is fed directly to the nozzle 1. The source bottle includes means for stirring such as a conventional stirring bar 4 and is placed on a heater and stirrer 5 to maintain uniformity within the solution. The spraying target 10 on support 11 is heated either directly by, for example, a regulated hot plate or indirectly with infrared lamp 13. Substrates placed in the target position and within the deposition field are heated to between 50 degrees C. and 150 degrees C. to afford rapid evaporation of the solvent after impingement and so as to prevent wetting of the substrate during deposition. Two shutters are shown in the figure. The primary shutter 6 is utilized to directly shield the substrates from the spray stream, and may be used to visually establish the pattern of the deposition field and alignment of substrates if necessary, and allow the spraying system to stabilize both dynamically and thermally before beginning the deposition. A remote shutter 8 may be used for the same purposes. To minimize gas turbulance in the system caused primarily by exhaust flow, a cylindrical air baffle 7 is used which aids in stabilizing the spray stream. The flow rate of the carrier gas is monitored by a flow meter 9 and regulated by a low pressure regulator 12. The spray deposition is contained within a clear plastic enclosure 15 which is vented by vent duct 16 which is isolated from the system by a conventional filter to minimize circular air turbulance in the area of the substrates, a shelf 13 isolates the upper part of the system from the lower part and helps provide support structure for the air baffle 7 and the shutters 6 and 8. An additional support 20 is contained in the container 15 for supporting the nozzle 1.

The source bottle 2 is graduated to aid in calibration and control of film thickness. All or part of the mixture solution may be sprayed. Varying the pressure within the source bottle by means of regulator 22 connected to a source of gas under pressure will alter the deposition rate. The deposition rate is controlled by any suitable means of controlling the solution flow rate and ultimately the mixing rate in the nozzle 1. The carrier gas can be any suitable gas such as air or nitrogen. Because the deposition process involves the evaporation of an organic solvent within the vented enclosure 15, certain flammability hazards may exist which may be minimized in an inert carrier gas. The carrier gas flow rate determines primarily the velocity and spatial distribution as well as the droplet size in the spray.

The described apparatus is illustrative only and modifications of this system to make the process continuous can be straight forwardly accomplished. For example, a modified apparatus could include a belt driven substrate track to increase throughput. A belt driven system would simplify loading of substrates which then could be external to the system. Additionally, a belt driven system could conceivably utilize several spraying steps in series as an in-line process for fabricating composite films.

After spray deposition is complete, the substrates are removed from the system and placed in a conventional annealing furnace. An annealing step at high temperature, usually several hundred degrees Centigrade and based on $\frac{1}{3}$ to $\frac{2}{3}$ of the temperature of the melting point of the metal-oxide, serves to remove any organic solvent which may be incorporated in the film, and serves to strengthen the film in terms of mechanical properties.

Figure 2:
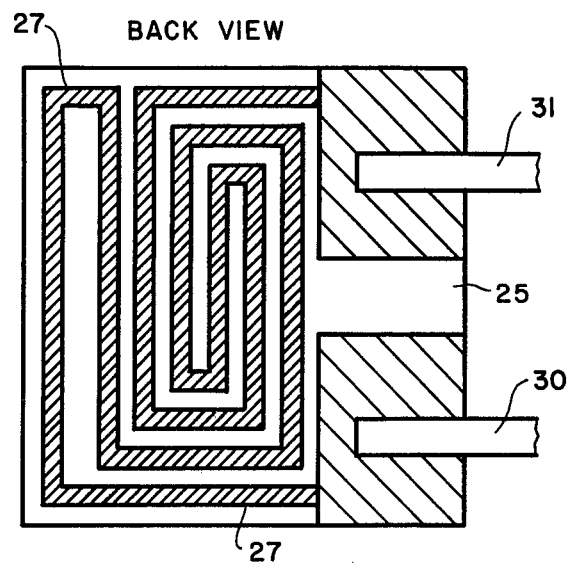
FIG. 2 is an illustration of a sensor comprising an interdigitated electrode structure disposed on a ceramic substrate and coated with a sprayed semiconductor film wherein a change in film electrical conductance upon exposure to gas can be measured.
Figure 2:
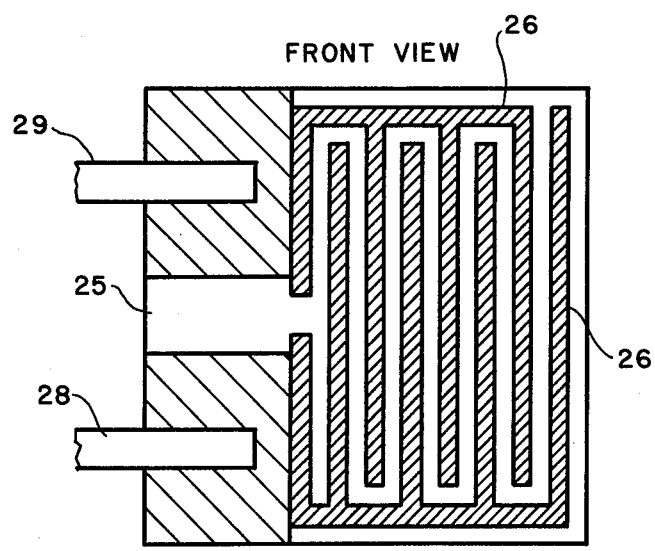

FIG. 2 illustrates an example of the substrate which can be used in the example of the present invention. The substrate is a ceramic base 25 with Platinum interdigitated electrodes 26 disposed on one side and a Platinum meandor pattern laser trimmed and used as a heating element 27 disposed on the opposite side. In operation, between 150 to 175 mA of electrical current is passed through the heater element which heats the sensor to between about 150 degrees C. to 200 degrees C. Platinum leads 28, 29, 30, 31 are attached providing electrical connection to the heater 30, 31 and interdigitated array 28, 29. A mechanical connection is reinforced by a ceramic coating (not shown) and the heater element is passivated for protection. The substrate is available from Rosemount Engineering Ltd. Platline Div., Sussex England.

Materials combinations useful in semiconductor gas sensors, particularly metal oxides in powder form such as $SnO_2$, $ZnO$, $Al_2O_3$, $Ga_2O_3$, $FE_2O_3$, $In_2O_3$ or mixtures thereof which are usually mixed with metal and nonmetal dopants or activators, and or binding materials and, as a preferred embodiment of the present invention, zeolite molecular sieve materials useful as agents for defining and/or enhancing porosity, are directly compatible with device fabrication by the process of the present invention.

EXAMPLE 1

A semi-conductor gas sensor was fabricated according to the process of the present invention which possessed less than 1 PPM sensitivity and relative selectivity for $H_2S$ gas in air with rapid response time, of the order of several seconds, and comparable recovery times. The source material used was a mixture containing approximately 70% by weight tin oxide with 24% by weight alumina activated with 1% Pt (available from Alfa Ventron Div. Thiokol Corp.) and 6.0% zeolite (available from Linde Div. Union Carbide Corp.). The powders are dehydration baked at 115 degrees C. for 120 minutes before weighing, then thoroughly mixed using standard laboratory procedures. The mixture is suspended in an organic solvent such as isopropyl alcohol and/or water or a mixture of the two forming a dilute solution of about 500:1 by volume liquid to solid mixture.

The mixture suspended in solution was sprayed using a spray nozzle model #¼JCO-SS obtained from Spraying Systems, Inc. North Ave. Wheaton, IL, at a carrier gas of nitrogen flow rate of about 3.0 liters/minute for proper spray velocity and spatial distribution to achieve a uniform deposition on the substrate. A circular deposition field was established with acceptable thickness uniformity over an area of about 30 mm dia. at a distance of about 30 cm from the nozzle. Such a deposition field can readily accomodate up to about 100, 2.5 mm by 2.5 mm substrates in one process deposition step. The substrates were heated prior to spraying to about 50 degrees C. and maintained at that temperature during deposition to assure rapid evaporation of the liquid. Under these conditions droplet impingement on the substrate was seen visually as an instantaneous event of droplet wetting of the substrate surface and evaporation. The dynamics of the process are stabilized as to prevent widespread wetting, accumulation, or puddling of the solution on the substrate.

A typical film thickness resulting was several hundred microns in thickness and was obtained by spraying for twenty to thirty minutes.

After spray deposition is complete, the film was annealed by heating at 700 degrees C. in air for twelve hours to remove residual solvents and strengthen the film. After annealing, film mechanical properties and adherance were satisfactory.

After completion of the sensor it can be used in a conventional manner in electronic equipment designed for relating changes in conductivity to specific gas concentrations. Such equipment normally employs circuitry for applying current and voltage to the substrate heater while measuring semiconductor conductance with conventional circuitry and coverting conductance to a gas concentration. As with other semiconductor gas sensors, conduction electrons in semiconducting metal-oxides such as tin oxide originate from shallow donor levels near the conduction band edge and from the release of trapped charge at surface acceptor states. Plotting electrical conductivity in air ($OHM^{-1}CM^{-1}$) versus inverse absolute temperature ($°K.^{-1}$) results in a curve where portions are approximately fitted by an expression of the form $\sigma = A \exp[-E_A/kT]$ where A is a material constant, T is absolute temperature, k is Boltzmann's constant and $E_A$ is the activation energy for conduction electrons in the material. The temperature regions of these curves corresponding to the region of operation of these sensors is fitted with values for $E_A$ ranging from 0.7 eV to 1.0 eV. These high activation energies have been attributed to thermal emission of trapped electrons from ionized surface acceptor states, thought to be ionized oxygen atoms. The predominant low temperature form of ionized oxygen is $O_2^-$. At higher temperatures above about 200 degrees C., $O^-$ and $O^{--}$ predominate. The presence of certain materials such as Pt reduces the $E_A$ of the surface acceptor levels.

The reaction involving $H_2S$ is believed to be described as follows. $H_2S$ gas reacts with chemically adsorbed ionized oxygen forming volatile products and freeing trapped electrons from the oxygen back to the solid. The result is conductivity modulation in the surface layers and at intergrannular contacts of the solid measured as an increase in conductivity.

For oxygen, the adsorption process is described as

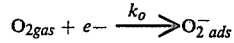

where $k_o$ is the reaction rate constant for chemisorption, and $e-$ is an electron from the solid.

Physically adsorbed $H_2S$ gas can move across the surface until it encounters an $O_2^-{}_{ads}$ (Langmuir process), or $H_sS$ gas can directly interact with $O_2^-{}_{ads}$ (Eley-Rideal process). The pertinant reaction is believed to be

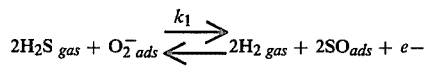

The rate constant for the reaction is $$k_1 = \frac{[H_2]^2 [SO]^2 [e-]}{[H_2S]^2 [O_2^-]}$$

The [] refer to concentration. For small concentrations of $H_sS$, $[O_2^-]$ can be considered a constant. Additionally, $$[H_2]^2 = [SO]^2 = [e-]$$

Therefore, $$[e-] = k'[H_2S]^{\frac{2}{5}}$$

We also have that the film conductivity, and thus its measured electrical conductance, G, are proportional to [e−].

$G = a[H_2S]^b$ is the expected dependence of conductance on $H_2S$ gas concentration in air with $b = \frac{2}{3}$. This is substantially the form observed. In actuality we have found that the exponent, b, and coefficient, a, can both be controlled to some extent by changes in film thickness, grain size and porosity, and dopant concentrations. The observed trends are not unexpected and suggest optimization of film properties for a given desired response characteristic. Following the foregoing analysis the process of the present invention can be adjusted to achieve this optimization.

Sensors fabricated in the herein described manner have been shown to be very well suited to detection of $H_2S$ gas in air with lower limit of sensitivity below 1 PPM. The sensitivity range of particular interest in health and safety monitoring and protection instrumentation is usually 0–50 PPM. In addition these sensors are not degraded by high concentrations of $H_2S$. Complete recovery after exposures as great as 1% $H_2S$ in air has been demonstrated. The response time for a typical sensor to 10 PPM $H_2S$ in air is less than 10 seconds to reach 90% of final value. The final value of resistance for 10 PPM $H_2S$ in air typically represents about 500× decrease in film resistance.

Interference data has been collected for several common interfering gases. These gases are $SO_2$, CO, $H_2$, Hexane, Methane, and aromated Propane. The sensor response to these gases at relatively high concentration is less than an equivalent response to 1 PPM $H_2S$. Additionally, the sensor response to changes in relative humidity is less than an equivalent response to 1 PPM $H_2S$. The selectivity is attributed in part to the relatively low temperature of operation and the presence of zeolite in the film.

What is claimed is:

1. A semiconductor sensor for specific gases comprising a multiple layered structure including an insulating substrate having a discrete semiconductor layer deposited thereon formed by spraying a liquid suspension of a mixture comprising a preselected solid metal/oxide semiconductor capable of sensing a specific gas and a porosity enhancing and defining agent capable of defining pore sizes in said layer of a predetermined size which is selected to permit a predetermined specific gas to come into contact with the semiconductor within said layer.

2. The article of claim 1 wherein said mixture of solids in addition contains a transition metal activator for the metal oxide semiconductor.

3. The article of claim 2 wherein said insulating substrate has deposited thereon at least two electrical contacts between the substrate and the semiconductor containing layer, said contacts being separated from each other and capable of being electrically connected through said semiconductor layer.

4. The article of claim 3 wherein said insulating substrate contains a resistance heating element incorporated therein which is physically separated from said electrical contacts and said semiconductor layer and capable of heating said substrate to a temperature in excess of 150° C.

5. The article of claim 1 wherein the porosity increasing and defining agent includes zeolite to define a predetermined pore size.

6. The article of claim 5 wherein at least 70% by weight of the semiconductor gas sensor layer is a gas sensing metal oxide.

7. The article of claim 6 wherein the metal-oxide is selected from the group of metal oxides including stannic oxide, zinc oxide, aluminum oxide, gallium oxide, ferric oxide, indium oxide, or mixtures thereof.

* * * * *